United States Patent [19]

Battista et al.

[11] Patent Number: 4,458,031

[45] Date of Patent: Jul. 3, 1984

[54] METHOD OF PREPARING A MAGNESIUM-MANGANESE CATALYST PRECURSOR AND CATALYST

[75] Inventors: Richard A. Battista, Albany; James G. Bennett, Jr., Glenmont; John J. Kokoszka, Delmar, all of New York

[73] Assignee: General Electric Company, Pittsfield, Mass.

[21] Appl. No.: 356,309

[22] Filed: Mar. 9, 1982

Related U.S. Application Data

[63] Continuation of Ser. No. 162,358, Jun. 24, 1980, abandoned.

[51] Int. Cl.$^3$ .................. B01J 21/10; B01J 23/34
[52] U.S. Cl. ..................... 502/324; 568/794
[58] Field of Search .............. 252/471; 568/794, 804; 502/324

[56] References Cited

U.S. PATENT DOCUMENTS

| | | | |
|---|---|---|---|
| 3,306,874 | 2/1967 | Hay | 528/215 |
| 3,422,156 | 1/1969 | Thoma | 568/804 |
| 3,446,856 | 5/1969 | Hamilton | 568/804 |
| 3,463,824 | 8/1969 | Velling | 568/804 |
| 3,748,282 | 7/1973 | Evans | 252/471 |
| 3,972,836 | 8/1976 | Van Sorge | 252/471 |
| 3,974,229 | 8/1976 | Van Sorge | 568/804 |
| 4,041,085 | 8/1977 | Frabetti | 568/804 |
| 4,201,880 | 5/1980 | Van Sorge | 568/804 |
| 4,227,023 | 10/1980 | Kawamata et al. | 568/794 X |

Primary Examiner—W. J. Shine
Attorney, Agent, or Firm—Hedman, Gibson, Costigan & Hoare

[57] ABSTRACT

Disclosed are a catalyst comprising a magnesium-containing moiety, a method for preparing the catalyst, and a process for the vapor phase ortho-alkylation of phenols in the presence of the catalyst.

8 Claims, No Drawings

METHOD OF PREPARING A MAGNESIUM-MANGANESE CATALYST PRECURSOR AND CATALYST

CROSS-REFERENCE TO RELATED APPLICATION

This is a continuation of application Ser. No. 162,358, filed June 24, 1980, now abandoned.

BACKGROUND OF INVENTION

This invention relates to a catalyst comprising a magnesium-containing moiety and a manganese containing moiety, to a method for preparing the catalyst, and to a process for the vapor phase ortho-alkylation of phenols in the presence of the catalyst.

Ortho-alkylation of phenols and catalysts therefor are well-known in the art and are described in Hamilton, U.S. Pat. No. 3,446,856; Van Sorge, U.S. Pat. No. 3,972,836; Van Sorge, U.S. Pat. No. 3,974,229; and in Frabetti U.S. Pat. No. 4,041,085. All of the above patents are incorporated here reference.

Although the catalysts and methods for preparation thereof described in the above patents are important advances in the art, there is room for improvements.

It has now been found that a highly effective ortho-alkylation catalyst containing a magnesium moiety and a manganese moiety can be prepared in efficient manner by a new method. In this method the source of the manganese of moiety is an aqueous solution of manganese nitrate. Such solution is included in formulating a reaction mixture which further includes a magnesium carbonate compound suspended therein. Heating the reaction mixture as herein described results in precipitation of manganese hydroxide onto the magnesium containing compound to form a composite precursor of the catalyst being formed. Advantageously, no washing step is required in preparing the catalyst by the method of this invention.

DESCRIPTION OF THE INVENTION

Generally stated, in one aspect this invention provides a method of preparing a magnesium-manganese catalyst useful for the ortho-alkylation of phenols, comprising:

(a) forming a reaction mixture comprising an aqueous solution of manganous nitrate and a magnesium compound suspended therein, said compound being basic magnesium carbonate, (B) heating the reaction mixture to a temperature of at least 100° F. for a period of time sufficient to precipitate manganous hydroxide onto the suspended magnesium compound, (C) separating at least a portion of the magnesium compound having manganous hydroxide precipitated thereon from the remaining reaction mixture.

(D) drying the separated portion, (E) forming finely divided particulate matter from the separated portion, (F) shaping the resulting dried portion into a preselected or desired shape, and (G) calcining the shaped portion at a temperature of from about 250° F. to about 1000° F. to form the catalyst.

In another aspect, generally stated, this invention is for the catalyst prepared by the method set forth above.

Generally stated, in another aspect this invention provides an improvement in the heretofore known process for selectively alkylating a phenol in the ortho position which comprises the vapor phase reaction in the presence of an alkylation catalyst of an alkyl alcohol and a phenol having the general formula

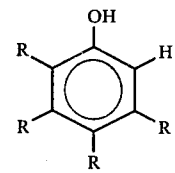

where each R is a monovalent substituent selected from the group consisting of hydrogen, alkyl, phenyl and alkyl-substituted phenyl. The improvement comprises conducting said reaction in the presence of a catalyst prepared by the method set forth above.

In another aspect, generally stated, this invention provides an improvement in the process of selectively producing 2,6-xylenol which comprises the vapor phase reaction in the presence of an alkylation catalyst of methanol with a mixture of phenol and c-cresol, the improvement comprising conducting said reaction in the presence of a catalyst prepared by the method set forth above.

In each of the above improvments, this reaction is preferably conducted in the further presence of water vapor.

DETAILED DESCRIPTION OF THE INVENTION AND MANNER AND PROCESS OF MAKING AND USING IT

In preparing the catalyst of this invention in accordance with the catalyst preparation method set forth above, the reaction mixture can be formed in any suitable manner. The reaction mixture may be formed, for example, by adding the magnesium compound to an aqueous solution of manganese nitrate, by adding manganese nitrate to an aqueous slurry or suspension of the magnesium compound, by adding the magnesium compound and the manganese nitrate to water, and the like. Preferably, the magnesium compound is suspended in water and an aqueous manganese nitrate solution is slowly added, with stirring to the aqueous slurry containing the magnesium compound.

The magnesium compound is preferably basic magnesium carbonate. The magnesium compound is preferably in finely divided particulate form having a high ratio of surface area to weight and high porosity.

Aqueous slurries wherein the suspended magnesium compound is present in any suitable amount may be employed. For example, the aqueous slurry may include from about 5 to about 35% by weight, preferably about 15%.

Where the manganese nitrate is added as an aqueous solution, the nitrate compound may be present therein in any suitable amount up to its solubility, and preferably about 5% by weight.

Any suitable molar ratio of magnesium to manganese may be employed in the reaction mixture. The value of such molar ratio is dependent on the magnesium to manganese ratio desired in the ultimately prepared catalyst. In general, the catalyst may include from about 0.022 to about 0.25 moles of manganese, preferably about 0.022 to about moles, per mole of magnesium. Preferably, the molar ratio of manganese to magnesium employed in the reaction mixture is about 1.1 times the theoretical molar ratio thereof desired in the ultimately prepared catalyst.

The reaction mixture is heated to a sufficient temperature, e.g. 100° F. and at least 140° F., and maintained thereat for a sufficient time to precipitate (i.e. deposit) manganous hydroxide onto the magnesium compound. In general, at a temperature of about 180° F., for about 2 hours or more is a suitable time, with longer time required at lower temperatures and shorter time acceptable at higher temperatures. Preferably, the heating is continued at any selected temperature for a time sufficient to precipitate substantially all the manganese initially present in the reaction mixture.

After the manganese hydroxide is precipitated onto the magnesium compound, at least a portion of the compound with the manganese hydroxide deposited thereon is separated from the balance of the reaction mixture by any suitable separation procedure, e.g. filtration, centrifuging, etc. Centrifuging is preferred for large-scale production. However, good results can be obtained using almost any known separation procedure.

Drying of the separated magnesium compound having manganese hydroxide deposited thereon may be effected in any suitable manner, using hot air, vacuum, combination thereof, etc. Preferably, drying is effected at temperatures below 200° F. to a sufficiently dry state (e.g. 2% volatiles or less, preferably 1% volatiles or less) such that the material can be pulverized to a substantially free-flowing particulate form.

After drying, the dried separated portion is formed into finely divided particulate form, as by grinding or the like, of preferably sufficiently small size to pass through a 16 to 20 mesh screen.

Thereafter, the particles are shaped to the desired physical form using any suitable shaping method and device. For example, the particles may be formed into tablets using a tabletting press and well-known tabletting procedures. The shaped particles may be in the form of pellets, Rashing rings, cylinders, tablets or any other shape known in the art.

After shaping, the shaped particles are calcined to form the catalyst of this invention. Calcination is effected at a temperature of about 250° F. or more, and preferably in the range from about 250° F. to about 1000° F.

Advantageously, calcination of the catalyst prepared by the method of this invention can be effected "in situ", i.e. in the reactor to be employed in effecting ortho-alkylation of a phenol in the presence of the calcined catalyst.

If desired, shaping aids (e.g. tabletting aids) and/or binders may be employed in preparing the catalyst. In the best mode for forming tablets, a minor amount (e.g. 0.5%) graphite is added to the particles prior to tabletting. If desired, polyphenylene oxide—described in Hay, U.S. Pat. Nos. 3,306,874 and 3,306,875—may be composited with the particles of catalyst being formed in amounts up to about 20% by weight to aid in binding the particles.

According to this invention ortho-alkylated phenols are formed by a process which comprises vapor-phase reaction of an alkyl alcohol, e.g., a saturated aliphatic alcohol such as methyl, ethyl, propyl, isopropyl, butyl, isobutyl, tert.-butyl, amyl isoamyl, hexyl, heptyl, octyl, nonyl, decyl, undecyl, lauryl, cetyl, cyclohexyl, and the like, alcohols, and especially preferably an alcohol containing up to 6 carbon atoms and most preferably methanol, and a phenol having at least one unsubstituted ortho position in the presence of the catalyst of this invention at a temperature of at least 300° C., and preferably at a temperature varying between 400° C. and 500° C., and especially preferably at 400° C. and 450° C. In general, the process conditions are similar to those disclosed in the above-noted Hamilton patent, but differ therefrom primarily in the substitution of the catalyst of this invention and by use of a lower reaction temperature.

While the invention has been described as applying specifically to phenols and ortho-cresol, it may be applied in general to any phenol having an ortho-hydrogen. For example, it also may be used with ortho-phenyl phenol, ortho-ethyl phenol, and phenols in which there are alkyl and aryl groups in the meta- and para-positions. These phenols may be represented by the formula:

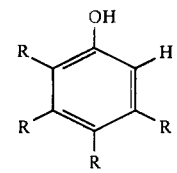

where each R is a monovalent substituent selected from the group consisting of hydrogen, alkyl, e.g., $C_1$–$C_{12}$ alkyl, phenyl and alkyl-substituted phenyl, e.g., $C_1$–$C_{12}$ alkyl-substituted phenyl.

In carrying out the alkylation in accordance with this invention, any one or a mixture of phenols having an ortho-hydrogen may be vaporized and passed through a reactor heated to a suitable temperature, e.g., at least 200° C., and preferably at least 300° C. containing the magnesium oxide-manganese oxides catalyst of the invention. In order to obtain the maximum yield of ortho-alkylate products, at least one mole of the alkyl alcohol and preferably from 1 to 3 moles of the alcohol are used for each ortho position on the phenol to be alkylated. For example, if phenol, which has two-ortho hydrogens per molecule, is to be methylated to produce a maximum yield of 2,6-xylenol, it is desirable to use two to six moles of methanol for each mole of phenol with higher yields being obtained with higher ratios of methanol to phenol.

The vapors issuing from the reactor are condensed and the product separated by conventional methods such as crystallization, distillation, etc. The reaction proceeds at atmospheric pressure, but pressures above or below may be used.

As will be apparent to those skilled in the art, the process can be carried out under a variety of reaction conditions. These conditions are temperature, pressure, flow rate of reactants, vapor space velocity of the reactants over the catalyst, contact time of the reactants with the catalyst, length of the catalyst bed, specific activity of the particular catalyst, etc. The effects of these reaction variables are those to be expected from a consideration of the technical aspects of the reaction involved. For example, the reaction of alcohol with the phenol compound to produce the desired ortho-alkylated products proceeds faster as the catalyst bed temperature is increased provided that the temperature is not so high that secondary reactions such as decomposition of the reactants or products occur to decrease the yield of desired product. Such secondary reactions do not occur to any appreciable extent in this reaction up to a temperature of about 500° C. Above 500° C., decomposition of the reactants and product becomes a proble because it deposits carbon on the catalyst, decreasing its activity. In contrast to prior art catalysts, in the range of from 275° C. to 500° C. when using a high proportion of methanol to phenol, i.e., 2-3 times the amount of methanol required to methylate each ortho-position of the phenol, the tendency to decompose methanol to gaseous products is decreased. Below a temperature of 200° C., the reaction of methanol with the phenol is so slow that the yield of product per hour per volume of catalyst is so low as to make the reaction uneconomical to carry out, regardless of the reaction conditions.

In accordance with well known techniques to compensate for lower rates of reaction, if, for example, less reactive phenolic compounds or alkanols are used, a longer contact time of the reactants with the catalyst can be used. This may be done by changing any one or several of the variables which decrease the vapor space velocity of the reactants over the catalyst, thus increasing the contact time. Examples of this are increasing the amounts of catalyst, decreasing the flow rate of reactants, increasing the pressure in the reactor, etc. At the lower flow rates, there is some tendency for the selectivity to decrease because the longer contact time does permit any product which has been completely substituted in the two ortho-positions in the initial part of the reaction to have time to react further to produce some para-substituted product. This loss in selectivity can be compensated by increasing the space velocity but not the flow rate of reactants by using an inert diluent for the reactants for example, an inert gas, i.e., nitrogen, argon, etc., or an inert vapor, i.e., benzene, toluene, etc., or by using a lower pressure in the reactor.

If it is desired to use pressure, the flow rate of the reactants can be increased to give an equal contact time. It, of course, will be recognized that it is possible to have a flow rate of reactants so great, either with or without pressure, that the effective contact time is reduced to an economically unsatisfactory level.

Generally, reaction conditions are chosen so as to minimize the amount of unreacted feed materials which must be recovered and reused. However, reaction conditions which on the face might appear undesirable from an over-all yield point of view may be desirable from an economic point of view because of the very high degree of selectivity of the reaction under such conditions to give exclusively only ortho-alkylated products. On the other hand, reaction conditions can also be adjusted to give high over-all yields in terms of pounds of ortho-alkylated product per hour per volume of catalyst when a very small yield of para-substituted product can be tolerated.

It will also be recognized that, because of differences in the specific activities of the catalysts, each particular catalyst will have different optimum reaction conditions than another catalyst. The more reactive the catalyst, the shorter the contact time needs to be to give the same degree of conversion to ortho-alkylated products. Therefore, a higher space velocity or a lower temperature may be used with a more reactive catalyst. It has been found that a catalyst which has not been used in the reaction or has been regenerated, has an induction period during which time the selectivity of the catalyst increases until it reaches a maximum which it maintains for a long period of time.

In the following examples, the reactor consists of a reservoir containing a solution of alcohol and phenol compound, connected to a metering pump which feeds the reactants through a ¼ inch stainless tube into a vertical vaporizer made from a 12-inch long piece of 1 inch O.D.×0.8 I.D. stainless steel tubing. The vaporizer is partially immersed in a bath of fused salt to a depth of about 6 inches. The vapors from the vaporizer are fed to an 0.8 inch I.D. stainless steel tybe reactor through a 1 inch length of 0.50 inch I.D. stainless steel pipe located 5.50 inches above the bottom of the vaporizer and connected to the reactor 13 inches from its bottom. The reactor is 24 inches long and is immersed in the fused salt bath to a depth of 14 inches. Since the inlet tube of the reactor coming from the vaporizer also passes through the fused salt bath, it serves as a preheater for the vapor issuing from the vaporizer to bring the vapor up to the temperature of the reactor. The reactor is equipped with a thermowell made from ⅛ inch stainless steel tubing concentrically located in the reactor and extending downwards into the catalyst bed to a depth of 1 to 6 inches. Thus the catalyst bed temperature can be measured throughout a large section of the tube. The bottom portion of the reactor tube is filled with about 20 ml. of glass beads and then 110 ml. of catalyst is introduced which fills the tube to a depth of 14 inches. The reactant vapors are fed to the top of the catalyst bed and product vapors leave the bottom of the reactor through a ⅜ inch O.D. stainless steel outlet tube. The product vapors are led to a water-cooled condenser and receiver.

This invention is further illustrated by the following illustrative, but non-limiting examples, wherein all amounts, parts and percents given are by weight unless otherwise indicated.

EXAMPLE 1

This example illustrates the catalyst preparation method and the improved ortho-alkylation process of the present invention.

Catalyst Preparation—Distilled water (2000 ml) was added to a 5000 ml round-bottom glass flask equipped with a thermometer and stirrer. The lower half of which was covered with a variac-controlled heating mantle. The water was heated to a temperature of 82° C. and then 518.9 grams of basic magnesium carbonate, $4MgCO_3.Mg(OH)_2.5H_2O$ (BMC) were added to the heated water with stirring to form a slurry with substantially all the added BMC suspended therein. While stirring was continued, nitrogen was blown over the slurry. While stirring and the nitrogen purge were continued, dropwise addition to the slurry of a dilute aqueous solution of manganous nitrate $Mn(NO_3)_2$ was begun. (The solution was prepared by diluting 40.0 grams of a 50% aqueous solution of the manganous nitrate by adding, with stirring, sufficient distilled water to form a 450 ml solution). The slow addition of the entire dilute manganous nitrate solution was completed in 4 minutes, 11 seconds.

The resulting reaction mixture or slurry containing the dilute nitrate solution with BMC suspended therein was stirred for 6 hours at 82° C. in a closed atmosphere with nitrogen blanketing the reaction mixture. The resulting suspension of BMC with manganous hydroxide precipitated or deposited thereon was separated from the balance of the reaction mixture by filtration thereof using a coarse fritted filter. The resulting wet cake (residue) was dried overnight (about 12-20 hours)

using an oven maintained at about 120° C. and subatmospheric pressure.

The resulting dried cake was ground to a fine powder using a mortar and pestle, followed by blending with a sufficient amount of polyphenylene oxide powder on a jar mill to form a pulverulent composite containing 80% powdered dried cake and 20% polyphenylene oxide. The pulverulent composite was compression shaped using a conventional press to form cylindrical tablets of about 1/16 inch in length to about 3/16 inch in diameter. The polyphenylene oxide, which is optionally included in the catalyst of this invention, was added as a binder.

A catalyst bed having an overall volume of 110 ml. is formed in the reactor tube of the reactor as described above by introducing such volume of the catalyst tablets. Thereafter, the reactor tube is capped and the reactor is immersed in the salt bath at 370° C. to the depth set forth above. Calcination of the catalyst is at least partially effected by passing nitrogen through the bath-heated catalyst bed at a volumetric rate corresponding to 2 SCFH (standard cubic feet per hour) for 15 minutes.

Testing—The catalyst was tested for catalytic performance in a continuous process for ortho-alkylation of phenolic compounds. The liquid feedstock which contained methanol, phenol, ortho-cresol and water, was continuously fed at a rate of 228 ml/hour throughout the 311-hour test. The resulting feed vapors were continuously passed through the catalyst bed as described above. The conditions and results of the test are set forth in Table 1.

TABLE 1

| Feed Composition | | | |
|---|---|---|---|
| Molar Ratio Methanol to Phenolic Compounds | 4:1 | | |
| Molar Ratio Phenol to Ortho-Cresol | 60:40 | | |
| Wt. % Water in Feed | 23 | | |
| Operating Conditions | | | |
| Temperature (°C.) | 440-453 | | |
| LHSV (hr$^{-1}$)$^a$ | 2.07 | | |
| Pressure (psig) | 0 | | |
| Phenolic Distribution (wt. %) | 195 HR$^b$ | 311 HR$^b$ | TWA |
| o-cresol | 19.95 | 16.90 | 21.92 |
| 2,6-xylenol | 70.08 | 73.18 | 65.77 |
| 2,4,6-mesitol | 4.89 | 4.56 | 6.05 |
| Phenol | 4.74 | 5.31 | 6.28 |
| Off Gas (wt. %) | .550 | .580 | .476 |

$^a$LHSV is the liquid hourly space velocity and defines the volume of liquid per volume of catalyst per hour
$^b$Temperature at the indicated elapsed time was 453° C.
$^c$Time-weighted average of numerous values obtained, at generally uniform intervals throughout the 311-hour test From the above Table, it can be seen that the alkylation takes place primarily in the ortho position and a substantially high percentage of 2,6-xylenol is prepared using the catalyst of this invention. The 2,6-xylenol has commercial importance for preparing poly(2,6-dimethyl-1,4-phenylene) ether, a preferred polyphenylene oxide for blending with styrenic resins as tought, for examples, in Cizek, U.S. Pat. No. 3,383,435. The ortho-cresol formed in the reaction and unreacted phenol may be recycled if desired.

EXAMPLE 2

This example is a comparative example showing the preparation and performance of a magnesium manganese phenol-alkylation catalyst not in accordance with this invention.

The catalyst preparation procedure was substantially the same as that of Example 1 except as set forth below. The slurry temperature was room temperature (i.2., about 20–25° C.) instead of 82° C. After adding the dilute aqueous solution of manganous nitrate, there was slowly added to the reaction mixture 500 ml of a solution prepared by diluting 10.8 grams of an aqueous 50% sodium hydroxide solution with the requisite amount of distilled water.

The resulting reaction mixture was stirred for one hour at room temperature. Intermediate the filtration and drying steps, 1500 ml of distilled water were poured onto the wetcake and, using a hand-held homogenizer, the cake was resuspended in the water. This reslurry was then vacuum filtered. This reslurry step was repeated four more times for a total of five reslurries and vacuum filtrations. A final reslurry with 1250 ml of acetone was done. After filtering this, the wetcake was dried overnight in a 120° C. vacuum oven as in Example 1. The foregoing procedure of repreated or multiple washings (i.e., reslurrying and filtration), which has been found necessary to produce an acceptable ortho-alkylation catalyst using the preparation method of this example, is not required in the present invention.

After drying, grinding, mixing with polyphenylene oxide, shaping into tablets and calcination (all as described in Example 1), the catalyst tablets of this example were tested using the same procedure, feed composition and operating conditions as set forth in Example 1. To improve the quality of the comparison, the testing of the catalyst tablets of both Ex. 1 and Ex. 2 was conducted simultaneously using two substantially identical reactors which were fed from the same feedstock source.

The phenolic distribution and off-gas results for this example are set forth in Table 2.

TABLE 2

| Phenolic Distribution (wt. %) | 195 HR$^b$ | 311 HR$^b$ | TWA$^c$ |
|---|---|---|---|
| o-cresol | 21.14 | 16.94 | 28.43 |
| 2,6-xylenol | 71.28 | 75.72 | 60.48 |
| 2,4,6-mesitol | 4.05 | 3.83 | 4.20 |
| Phenol | 3.54 | 3.51 | 6.86 |
| Off Gas (wt %) | .470 | .520 | .378 |

$^b$Temperature at the indicated elapsed time was 453° C.
$^c$Time-weighted average of numerous values obtained, at generally uniform intervals throughout the 311-hour test.

Comparison of the phenolic distributions in Tables 1 and 2 shows that the catalyst of this invention is superior to the control catalyst (ex. 2) in catalyzing the preparation of 2,6-xylenol in long runs. Such superiority is evidenced by comparing the 65.77% 2,6-xylenol in the TWA(time-weighted average) column of Table 1 with the 60.48% 2,6-xylenol in the TWA column of Table 2.

What is claimed is:

1. A method of preparing a magnesium-manganese catalyst precursor useful after activation for the ortho-alkylation of phenolic compounds, comprising:
   (A) forming a reaction mixture comprising an aqueous solution of a soluble manganous salt and a magnesium compound suspended therein, and
   (B) heating the reaction mixture to a temperature and for a period of time sufficient to precipitate manganous hydroxide onto the suspended magnesium compound.

2. The method of claim 1, which comprises the additional steps of:

(C) separating at least a portion of the magnesium compound having manganous hydroxide precipitated thereon from the remaining reaction mixture,
(D) drying the separated portion,
(E) forming finely divided particulate matter from the separated portion,
(F) shaping the resulting dried portion into a preselected or desired shape, and
(G) calcining the shaped portion at a temperature of from about 250° F. to about 1000° F. to form an activated catalyst.

3. The method of claim 2 wherein the calcining step is performed in a reactor prior to effecting an ortho-alkylation reaction of a phenol in the presence of the catalyst in said reactor.

4. The method of claim 2, further including the step of forming an intimate admixture of the finely divided particulate matter formed in said step E with finely divided polyphenylene ether such that said ether constitutes a binder for the magnesium compound in the subsequently calcined catalyst.

5. The method of claim 1, in which the catalyst precursor includes from about 0.022 to about 0.25 moles of manganese for each mole of magnesium.

6. The method of claim 1, in which the reaction mixture is heated to a temperature of at least 140° F.

7. The method of claim 2, in which in step (D) the drying is effected at a temperature below 200° F.

8. The method of claim 7, in which the material after drying has a volatiles content of 2 percent or less.

* * * * *